United States Patent
Kallos et al.

(10) Patent No.: US 10,969,528 B2
(45) Date of Patent: Apr. 6, 2021

(54) METAMATERIAL OPTICAL FILTER AND METHOD FOR PRODUCING THE SAME

(71) Applicant: Metacontinental Inc., Dartmouth (CA)

(72) Inventors: Efthymios Kallos, Halifax (CA); Georgios Palikaras, Halifax (CA); John Cormier, Halifax (CA); Michael Wenyon, New York, NY (US); Andrew Yick, Woodland HIlls, CA (US); Thierry Leger, Beauzelle (FR)

(73) Assignee: Metacontinental Inc., Dartmout (CA)

( * ) Notice: Subject to any disclaimer, the term of this patent is extended or adjusted under 35 U.S.C. 154(b) by 360 days.

(21) Appl. No.: 15/653,374

(22) Filed: Jul. 18, 2017

(65) Prior Publication Data
US 2018/0031749 A1 Feb. 1, 2018

(30) Foreign Application Priority Data
Jul. 29, 2016 (GB) ..................................... 1613182

(51) Int. Cl.
*G02B 5/32* (2006.01)
*A61F 9/02* (2006.01)
(Continued)

(52) U.S. Cl.
CPC ................ *G02B 5/32* (2013.01); *A61F 9/022* (2013.01); *B64C 1/1476* (2013.01);
(Continued)

(58) Field of Classification Search
None
See application file for complete search history.

(56) References Cited

U.S. PATENT DOCUMENTS

| | | | |
|---|---|---|---|
| 4,608,578 A | 8/1986 | Balasubramanian | |
| 4,818,045 A * | 4/1989 | Chang | G02B 27/0103 359/13 |

(Continued)

FOREIGN PATENT DOCUMENTS

| | | |
|---|---|---|
| EP | 0036298 A1 | 5/1983 |
| EP | 1519249 A2 | 3/2005 |

(Continued)

OTHER PUBLICATIONS

Gi Ho Park et al, "The effects of graphene on the properties of acrylic pressure-sensitive adhesive", Journal of Industrial and Engineering Chemistry, Korea, vol. 20, No. 6, pp. 4108-4111 (2014).

(Continued)

*Primary Examiner* — Derek S. Chapel
(74) *Attorney, Agent, or Firm* — McDonnell Boehnen Hulbert & Berghoff LLP

(57) ABSTRACT

A metamaterial optical filter including: a transparent substrate; and a photosensitive polymer layer provided to the transparent substrate, wherein the photosensitive polymer layer is treated using a laser to form a non-conformal holographically patterned subwavelength grating, the holographic grating configured to block a predetermined wavelength of electromagnetic radiation. A system and method for manufacturing holographically patterned subwavelength grating onto the photosensitive polymer layer including: applying a photosensitive polymer layer to a transparent substrate; placing the photosensitive polymer layer between a laser and a mirror; scanning the laser over the photosensitive polymer layer such that a holographic grating is created within the photosensitive polymer layer by interaction between the laser light and light reflected from the mirror; and stacking two or more holographically patterned (Continued)

subwavelength grating layers to form complex metamaterial optical filter stacks.

21 Claims, 19 Drawing Sheets

(51) Int. Cl.
G03H 1/26 (2006.01)
G03H 1/02 (2006.01)
G02B 1/00 (2006.01)
G02B 5/18 (2006.01)
G02B 5/20 (2006.01)
G03H 1/04 (2006.01)
G02B 5/26 (2006.01)
B64C 1/14 (2006.01)

(52) U.S. Cl.
CPC ............ *B64C 1/1492* (2013.01); *G02B 1/002* (2013.01); *G02B 5/1809* (2013.01); *G02B 5/1857* (2013.01); *G02B 5/203* (2013.01); *G02B 5/26* (2013.01); *G03H 1/0244* (2013.01); *G03H 1/0248* (2013.01); *G03H 1/0402* (2013.01); *G03H 1/265* (2013.01); *G03H 1/024* (2013.01); *G03H 2001/0264* (2013.01); *G03H 2001/0439* (2013.01); *G03H 2223/15* (2013.01)

(56) References Cited

U.S. PATENT DOCUMENTS

| | | | | |
|---|---|---|---|---|
| 4,995,685 A * | 2/1991 | Armstrong | ............. | G03H 1/202 359/3 |
| 5,103,323 A | 4/1992 | Margarinos | | |
| 5,576,853 A * | 11/1996 | Molteni | ................. | G03H 1/202 359/12 |
| 5,721,630 A * | 2/1998 | Horner | ................. | G02B 5/0252 359/10 |
| 6,055,075 A * | 4/2000 | Nishikawa | ........... | G02B 5/1876 359/12 |
| 6,127,066 A * | 10/2000 | Ueda | .................... | G03H 1/0236 359/25 |
| 8,097,465 B2 * | 1/2012 | Millington | ............. | G01N 21/75 430/1 |
| 2007/0115522 A1 | 5/2007 | Ueda et al. | | |
| 2007/0206252 A1 | 9/2007 | Sissom | | |
| 2008/0213541 A1 * | 9/2008 | Schilling | .................. | B44C 1/00 428/161 |
| 2009/0162756 A1 | 6/2009 | Staub et al. | | |
| 2010/0231997 A1 * | 9/2010 | Fontecchio | ......... | G02F 1/13342 359/3 |
| 2010/0283957 A1 | 11/2010 | Matera | | |
| 2011/0098033 A1 | 4/2011 | Britz et al. | | |
| 2012/0099856 A1 | 4/2012 | Britz et al. | | |
| 2014/0329172 A1 | 11/2014 | Hart et al. | | |
| 2015/0338683 A1 | 11/2015 | Perricone | | |
| 2018/0188690 A1 * | 7/2018 | Kobrin | ................... | G03H 1/202 |

FOREIGN PATENT DOCUMENTS

| | | |
|---|---|---|
| WO | 2012000979 A1 | 6/2010 |
| WO | 2013054115 A1 | 4/2013 |
| WO | 2013166414 A2 | 11/2013 |
| WO | 2016012813 A2 | 1/2016 |

OTHER PUBLICATIONS

Combined Search and Examination Report issued in co-pending GB Patent Application No. GB1613182.3, UK Intellectual Property Office, dated Jan. 26, 2017, 3 pages.
International Search Report of International Application No. PCT/US2017/043389 dated Feb. 15, 2018.

* cited by examiner

METAMATERIAL OPTICAL FILTER AND METHOD FOR PRODUCING THE SAME

CLAIM OF PRIORITY

This Application claims the priority benefit of United Kingdom Patent Application Number 1613182.3, filed Jul. 29, 2017, the entire contents of which are incorporated herein by reference.

FIELD

This document relates to an optical filter and method for producing the same, and in particular a nano-patterned optically transparent thin film that can filter specific narrow optical frequencies.

BACKGROUND

Optical filters are used for many purposes, including for protection of eyes in various situations. One example of using filters to protect the eyes is in laser applications.

Laser Protection Systems (LPSs) are routinely used in laboratories around the world. LPSs typically come in the form of goggles or eyeshields which are worn by those present during the use of laser radiation. LPSs also come in the form of flat windows which are placed around the laser location to protect the surroundings. These filters are usually built using polymers and dyes (for low intensity lasers) or glass (for high heat densities).

There are several technical issues regarding currently available LPSs that affect their feasibility in other applications, such as, for example, aviation. First, LPSs usually operate to provide protection for a single bandwidth of light such as green or blue, providing protection from a single laser waveband only. Second, LPSs are not generally narrowband, i.e. limited to just the bandwidth of the laser in use. This means that the LPS will generally block more light than necessary and thus distort the overall vision while reducing the overall light transmission. Third, LPSs are usually color tinted, which once again distorts visual perception. Fourth, glass-based filters are heavy and can add weight or cannot be comfortably worn by individuals over an extended period of time.

While Bragg-based narrow interference filters made with deposition (e.g. sputtering) have become available in laboratory environments, these Bragg-based narrow interference filters tend to have poor angle optical performance, can flake and delaminate, tend to be color tinted and may distort the visual spectrum.

As such, there is a need for improved optical filters and methods for producing same.

SUMMARY

According to a first aspect herein, there is provided a metamaterial optical filter including: a transparent substrate; and a metamaterial film provided to the transparent substrate. The metamaterial film is configured to block a predetermined bandwidth of electromagnetic radiation at a predetermined angle range. The metamaterial film can consist of one or more photosensitive polymer nano-patterned layers provided to the transparent substrate, wherein each photosensitive polymer layer is treated, for example, using a laser, to include a holographically patterned subwavelength grating, the grating including non-conformal fringes. The optical filter may be used in various applications including aircraft windows (cockpit windshields), train windows/windshields, boat windows, car windows, building windows, test equipment windows, eyewear and visors. It will be understood that the predetermined bandwidth of electromagnetic radiation may be a single wavelength of electromagnetic radiation. Holographic gratings are sometimes referred to as notch filters.

According to another aspect herein, there is provided a metamaterial optical filter including: a transparent substrate; and a photosensitive polymer layer provided to the transparent substrate, wherein the photosensitive polymer layer includes a holographically patterned subwavelength grating, the grating including non-conformal fringes configured to block a predetermined bandwidth of electromagnetic radiation at a predetermined angle.

In a particular case, the holographically patterned subwavelength grating may be curved in order to maximize an effective angle of protection.

In another case, the holographically patterned subwavelength grating may include a plurality of gratings, wherein each of the gratings may be configured to block a different predetermined bandwidth of electromagnetic radiation. In this case, at least one of the plurality of holographically patterned subwavelength gratings may be provided to color balance the filter. Further, the plurality of holographically patterned subwavelength gratings may be configured to selectively block at least one of approximately 405 nm, 445 nm, 520 nm, 532 nm, 635 nm, 650 nm wavelengths.

In yet another case, the photosensitive polymer layer may be shaped for the transparent substrate using thermoforming and the photosensitive polymer layer may be pre-configured to allow for changes to the photosensitive polymer layer during thermoforming.

In still another case, the photosensitive polymer layer may be infused with a dye selected to color balance the filter.

In still another case, the metamaterial optical filter may further include a supplemental substrate that contains a dye selected to color balance the filter.

In yet still another case, the transparent substrate may include two or more transparent substrates and the photosensitive polymer film may be positioned between at least two of the two or more transparent substrates.

In yet another case, the predetermined angle of the non-conformal fringes may be up to 75 degrees below a normal axis of the filter.

In still another case, the electromagnetic radiation is optical radiation from a laser.

In yet still another case, metamaterial optical filter may further include an adhesive to bond the transparent substrate and photosensitive polymer layer or photosensitive polymer layers, wherein the adhesive may include graphene.

In still another case, the transparent substrate may selected from one of the following a window, eyewear, and a visor.

According to another aspect herein, there is provided a system for manufacturing a metamaterial optical filter, the system including: a clamp for holding a photosensitive polymer layer applied to a mirror; a laser; and a laser transport system for moving the laser relative to the photosensitive polymer film such that, as the laser moves over a surface of the photosensitive polymer film, laser light is reflected off of the mirror to create a holographically patterned subwavelength gratings within the photosensitive polymer layer.

In a particular case, the laser transport system may include: a carriage for carrying the laser; and rails provided adjacent the surface of the photosensitive polymer layer such that the carriage movably engages with the rails and is configured to move across the surface of the photosensitive polymer layer. In this case, the carriage and rails may be configured to move the laser in the longitudinal direction and the clamp may be configured to move the photosensitive polymer layer in the latitudinal direction.

According to another aspect herein, there is provided a method of manufacturing a metamaterial optical filter, the method including: applying a photosensitive polymer layer to a substrate; placing the photosensitive polymer layer between a laser and a mirror; and scanning the laser over the photosensitive polymer film such that a holographically patterned subwavelength grating is created within the photosensitive polymer layer by interaction between the laser light and light reflected from the mirror.

In a particular case, the scanning may include moving one or more of the laser, the photosensitive polymer layer and the mirror.

In another case, the method for manufacturing may further include thermoforming the photosensitive polymer layer to have a repeatable filter wavelength shift and a filter wavelength pre-compensation of the photosensitive polymer layer such that the thermoformed photosensitive polymer layer meets predetermined requirements. In this case, the original photosensitive polymer layer's bandgap may be pre-shifted to longer wavelengths in order to counter-balance the shift caused by the thermoforming process. Further, the bandgap pre-shift may be radially dependent with gradually smaller shifting away from the center of the photosensitive polymer layer.

In yet another case, the laser may be split into separate beams and the beams may be directed onto the photosensitive polymer layer at different angles of incidence.

In still another case, the laser may include a plurality of lasers of different wavelengths that are combined into a single combined beam and the combined beam may be directed onto the photosensitive polymer layer at a predetermined angle of incidence allowing notch filters of different wavelengths to be recorded simultaneously.

In yet still another case, each holographically patterned subwavelength grating formed on a single photosensitive polymer layer may be re-combined into a multi-layered metamaterial optical filter stack, including at least two or more holographically patterned gratings to allow control of angle, bandgap, optical density and color balance of the multilayered metamaterial optical filter stack. In this case, the method for manufacturing may further include an adhesive to bond the multi-layered metamaterial optical filter stack wherein the adhesive may include graphene.

BRIEF DESCRIPTION OF THE DRAWINGS

The following figures illustrate various aspects and embodiments of the metamaterial filter and system and method of manufacture herein.

DETAILED DESCRIPTION

Metamaterials have been proposed as a new type of optical filter for various applications (see, for example PCT Publication No. WO/2013/054115, Application filed Oct. 10, 2012). Nano-patterned multi-layered gratings can be designed for the development of transparent, ultra-thin optical filters. One additional example of a metamaterial film, in addition to those disclosed in the noted PCT application is a photosensitive polymer layer based on the Covestro™ Bayfol™ material, or one of its derivatives.

Figure 1:
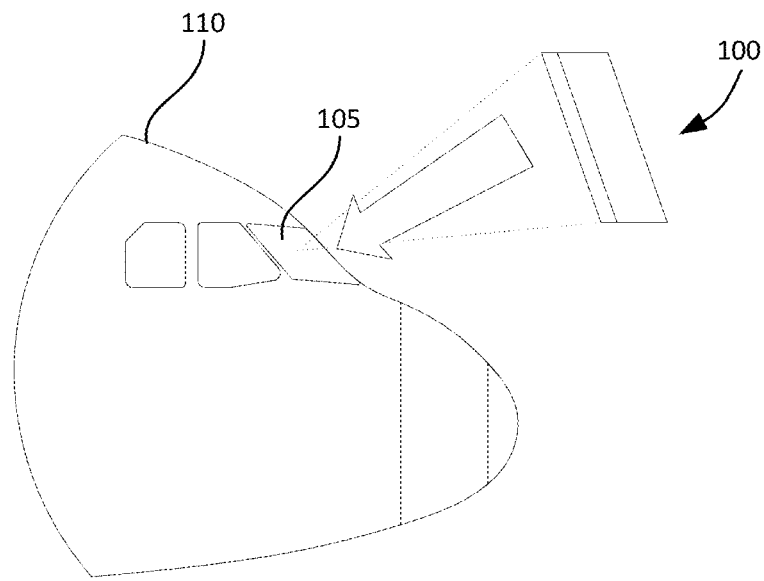
FIG. 1 illustrates an embodiment of a metamaterial film applied to an aircraft windshield.

These metamaterial filters can be applied to aircraft cockpit windscreens in order to selectively block light from, for example, laser attacks, which are a growing concern in the aviation industry. A bright visible laser light causes distraction or temporary flash blindness to a pilot, during a critical phase of flight such as landing or takeoff. It is far less likely, though still possible, that a visible or invisible beam could cause permanent harm to a pilot's eyes. These metamaterial filters have the advantage that only a narrow band of light is blocked so that the aircraft crew retain good visibility through the windscreen while being protected from a possible attack especially during night time operation FIG. 1 shows an example of a metamaterial formed as a nano-patterned, optically transparent film 100 that is applied to a windshield in an aircraft application. The metamaterial film 100 is typically applied on a surface of the glass cockpit window 105 of an airplane 110. It will be understood that the embodiments of the metamaterial filter and system and method herein may also be applied to or used in various applications including: eyewear, visors for helmets, heads up displays, or the like; windows of houses, buildings or the like; as well as with windscreens or windshields of other vehicles including cars, trucks, trains, boats, other aircraft such as helicopters, unmanned air vehicles, and the like. Further, in some applications the metamaterial film may be applied between glass panes/layers of a multi-layer windscreen, window, eyewear, visor or the like.

The metamaterial optical filter generally includes an optically clear adhesive film layer that can be applied on to the surfaces of eyeglasses, cockpit windscreens and other transparent surfaces. The metamaterial filter is generally transparent to all incoming light in the visible spectrum with the exception of certain wavelengths that are simultaneously and largely reflected by, and attenuated or partially absorbed inside by, the filter layers and its subwavelength gratings, protecting the persons behind the filter. The filters provide protection from electromagnetic radiation, such as optical spectrum wavelengths, including laser wavelengths, in a passive manner (i.e. without requiring a power source).

One of the difficulties with optical filters of the type described above relates to the complexity of making the thin film filters large enough and easily integrated for various applications such as windscreens and the like. One particular method for creating the nano-patterned sub-wavelength gratings inside the metamaterial film is using holography. Holography or photorefraction offers the possibility of a fabrication method where even complex large area films can be manufactured quickly, for example, in minutes.

Figure 2:
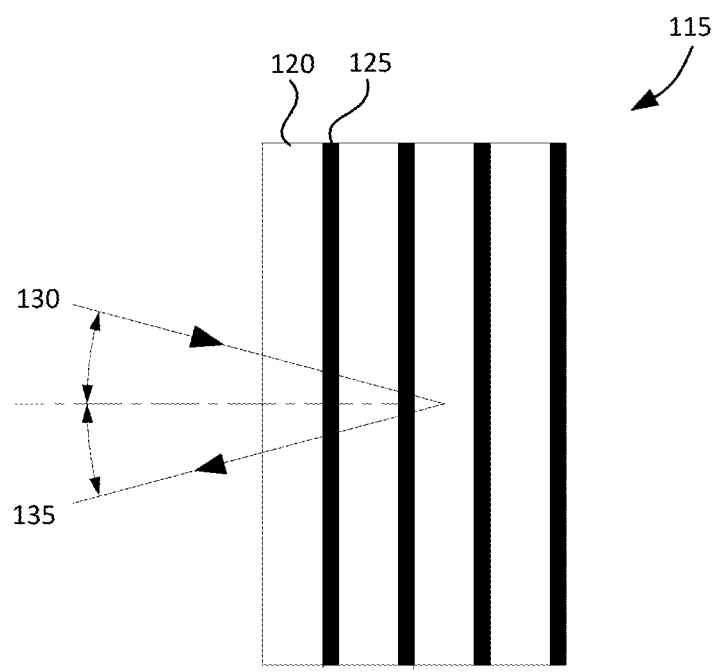
FIG. 2 illustrates a principle of a reflective filter made using a grating.

A photorefractive material has the property that its refractive index can be modified based on incident laser radiation. In the simplest scenario, the sample is placed against a mirror and illuminated with a laser. The interference intensity pattern created inside the photorefractive material causes changes in its refractive index, which can be tuned to match a desired refractive index pattern, creating a Bragg type mirror or Bragg grating. FIG. 2 illustrates the principle involved in creating the interaction of a Bragg type mirror with a laser. The Bragg type mirror/grating 115 is depicted as alternating layers of high 120 and low 125 refractive index gratings of predetermined thicknesses (based on the wavelength of radiation to be blocked). Typically, dozens or hundreds of layers are required, but only a few are shown in this illustration for clarity. Once the Bragg grating has been created, when a laser beam 130 is incident at an angle that is close to perpendicular to the Bragg grating direction, constructive interference effects cause the laser beam to be reflected back 135 (i.e. filtered).

Further, metamaterial filters made using holographically patterned subwavelength gratings can offer the wavelength selectivity of a dielectric filter, with the added advantage of a continuously-variable refractive index in the photosensitive polymer layers. This property is expected to increase the efficiency and wavelength selectivity. Metamaterial filters made using holographically patterned subwavelength gratings also offer dielectric layers that can tilt or curve with optical power normally only seen in refractive optics. Metamaterial notch filters can be optical elements that also bend or focus light.

Photosensitive polymer layers in particular can be made in thick layers (greater than 6 microns) because they require no access for wet developing chemicals; thicker layers can mean greater efficiency and even narrower wavelength selectivity (narrower bandwidth). Metamaterial filters made using multi-layered holographically patterned subwavelength gratings appear to offer the ability to filter out the near-theoretical minimum bandwidth to block a laser line and therefore exhibit lowest impact on the overall transmitted spectrum and color perception.

Metamaterial filters can be formed as parallel-fringe holographically patterned subwavelength gratings or as slanted-fringe holographically patterned subwavelength gratings. Both may be effective as tunable filters. However, from the point of view of mass production, there are major practical differences between making a slanted-fringe grating and a non-slanted one (where the fringe planes lie parallel to the surface).

Slanted-fringe gratings require either the presence of the full arrangement of optical components needed to generate the specific wavefronts required, or the ability to 'fix' this arrangement once it has been assembled in, for example, the laboratory. This requirement to have the full arrangement available is typically achieved by recording it in a 'master' grating layer that is then used to make further contact copies.

Slanted-fringe grating manufacturing could be done for a part such as a 'goggle lens' with the lens itself manufactured complete with an attached layer of unexposed photosensitive polymer in the production machine. Optical components could generate the necessary and possibly complex reference and subject beams and a robotic mechanism would present the part to the exposure station and remove it for further steps. Another possibility is to bring the blank lens together with its photosensitive polymer laminate—before or after exposure—within the manufacturing machine. Still further integration may be possible if the production machine molds the lens in plastic while the photosensitive polymer layer is inserted within it or applied after cooling. An integrated approach may be necessary if the photosensitive polymer layer needs to be curved in one or two dimensions either during or after recording (or both).

If the slanted-fringe grating can be made as an original 'master' grating layer, then it can be copied optically by scanning it with a single line of laser light running across the direction of the 'web'. This would be used if the master grating layer is either wrapped around the outside of a solid drum (if a reflection grating) or on the outside of a transparent drum illuminated by a line of laser light from the inside (if a transmission grating).

Scanning by a line of laser light is also sometimes employed when the slanted-fringe 'master' grating layer is copied lying flat, which by its nature requires that a step and repeat procedure is used. But if step and repeat is used—that is, the master and the copy are fixed in space over their entire surface area for a substantial time—then the whole surface of the master grating layer can be illuminated at the same time, limited only by the power of the laser.

In either case, a flat master grating layer copied by step and repeat may be needed for very large-area metamaterial filters, such as for an aircraft windshield.

Non-slanted fringe gratings for notch filters, also called 'holographic mirrors' because of both their appearance and the way they are made, are simpler to manufacture because they can tolerate motion in the plane of the recording medium during the exposure: specifically, if the recording medium moves parallel to the fringe planes during exposure, then the fringes are not blurred and can still be recorded with good contrast and grating efficiency. In practice, a machine to make such a nano-patterned subwavelength grating can tolerate 'slippage' of the photosensitive polymer layer in its own plane and this property has been used industrially to manufacture large-area seamless notch filters where the laser and a flat mirror behind the photosensitive polymer layer create a 'stack' of local interference fringes through which the moving web intentionally passes through.

In manufacturing volume gratings, the complex arrangement of many optical components on a vibration-isolated table can sometimes be replaced by a 'master' grating layer that is copied by a single expanded laser beam or a scanned line of laser light. Typically, an efficient hologram is needed for a 'reflection' grating, or a weak one (50% efficiency) for a transmission grating, but in either case it will be necessary that the grating can be copied by a collimated beam of laser light, which may be a limitation for complex metamaterial notch filter designs.

To manufacture relatively thick, so-called 'volume grating, it is necessary to establish an optical interference pattern stably fixed within the photosensitive polymer layer for the duration of the exposure time. A volume grating gets its name because it is thick enough to record a three-dimensional volume of interference fringes: for example, a 14-micrometer thick photosensitive polymer layer can record more than two dozen half-wave fringe layers. Unlike the mechanical embossing process used to reproduce the silver security holograms on credit cards, a coherent illumination source, such as a laser, is a necessary part of the production line to generate the 'live' interference pattern. Laboratory lasers are readily available with the necessary optical properties to make metamaterial filters using holographically patterned subwavelength gratings, but the finite limit on the power of actual lasers may set the upper limit on the speed of any manufacturing process.

The recording medium should preferably have high spatial resolution, for example, from approximately 1000 lines per mm and higher, and low noise or scattering so the resulting metamaterial filter has a glassy transparency. On the production line, a degree of mechanical stability is required during the moments of exposure. The material should be sufficiently sensitive that the effective exposure time can be short enough to ensure no movement on scales less than the wavelength of light.

Most nano-patterned and/or Bragg-style laser filters have inherently narrow operation in terms of the angle of the incident laser light. This is because the angle of operation is linked to the bandgap of the filter for a traditional periodic (high and low index) design: as the bandgap is reduced, the angle of incidence (AOI) for which the bandgap appears is reduced as well. Interestingly, this issue can be solved by curving the gratings of the metamaterial film such that their radius of curvature is centered at the location where the eye receiving radiation is expected to be found. This can be achieved by placing the photosensitive polymer layer on a curved substrate mold (with, for example, radius of curvature Rm) that may sit on top of a flat mirror. The substrate mold should be index-matched to the photosensitive polymer to provide maximum grating formation efficiency and suppress any unwanted effects. If the polymer then is bent by a radius of curvature Rp, the effective radius of curvature will be $1/(1/Rp-n/Rm)$, n being the average refractive index of the photosensitive polymer layer.

Figure 3C:
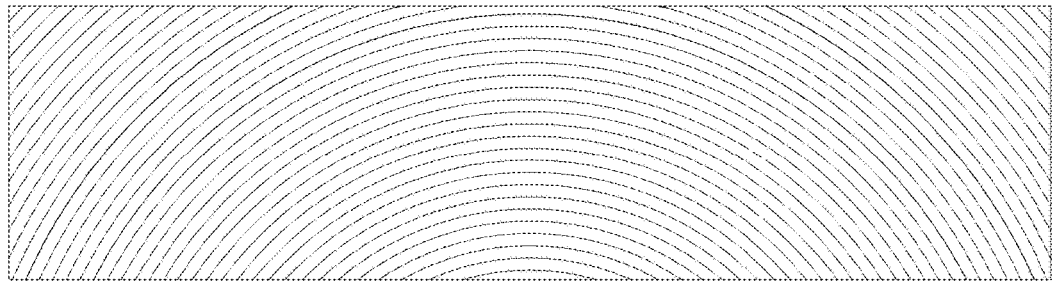
FIGS. 3A, 3B, 3C illustrate different types of holographically patterned subwavelength gratings.
Figure 3B:
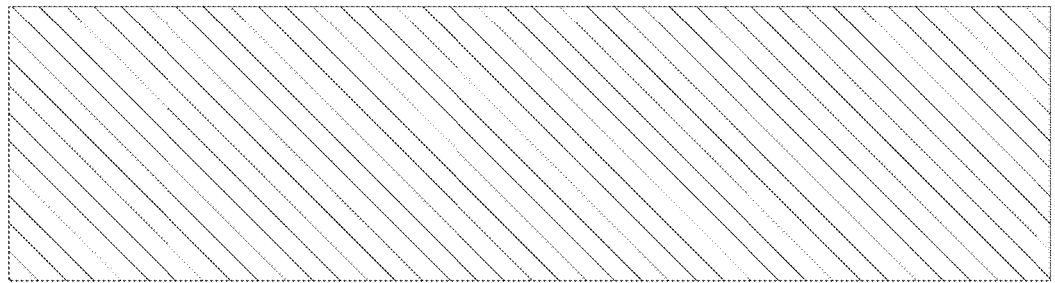
Figure 3A:
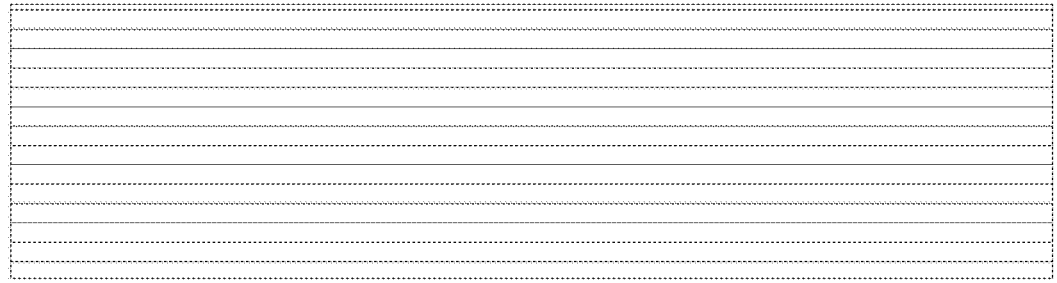
Figure 4:
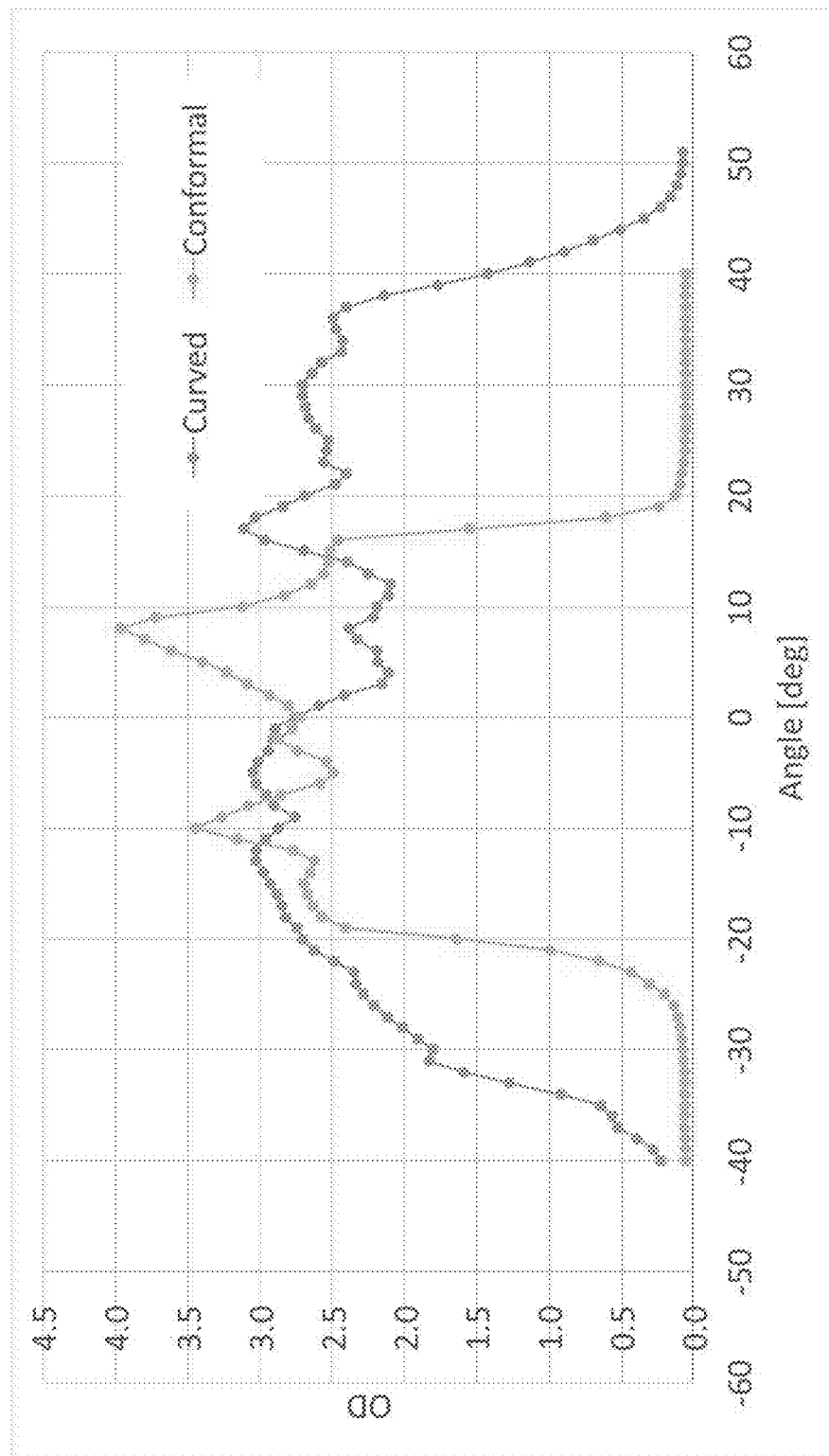
FIG. 4 illustrates angle coverage achieved with an example of holographically patterned subwavelength curved grating on a photosensitive polymer layer.

FIG. 3 shows various types of grating layers: a parallel (non-slanted or conformal) grating (FIG. 3A); a slanted (fixed-slant) grating (FIG. 3B) and a curved grating (FIG. 3C). For a curved grating layer, the holographically patterned subwavelength curved grating may be formed such that, on a flat surface, the grating has a main axis (k-vector) that varies in angle as a function of the position along the metamaterial film. For example, for each horizontal location in the metamaterial film (x-axis) a 40° AOI may be achieved (where the optical density is greater than 2.0) but this AOI will be centered around a different angle along the length of the metamaterial film. The curved grating allows for a larger protection angle, as illustrated in FIG. 4, where more than 60° angle coverage is achieved with an example curved grating layer.

Figure 5:
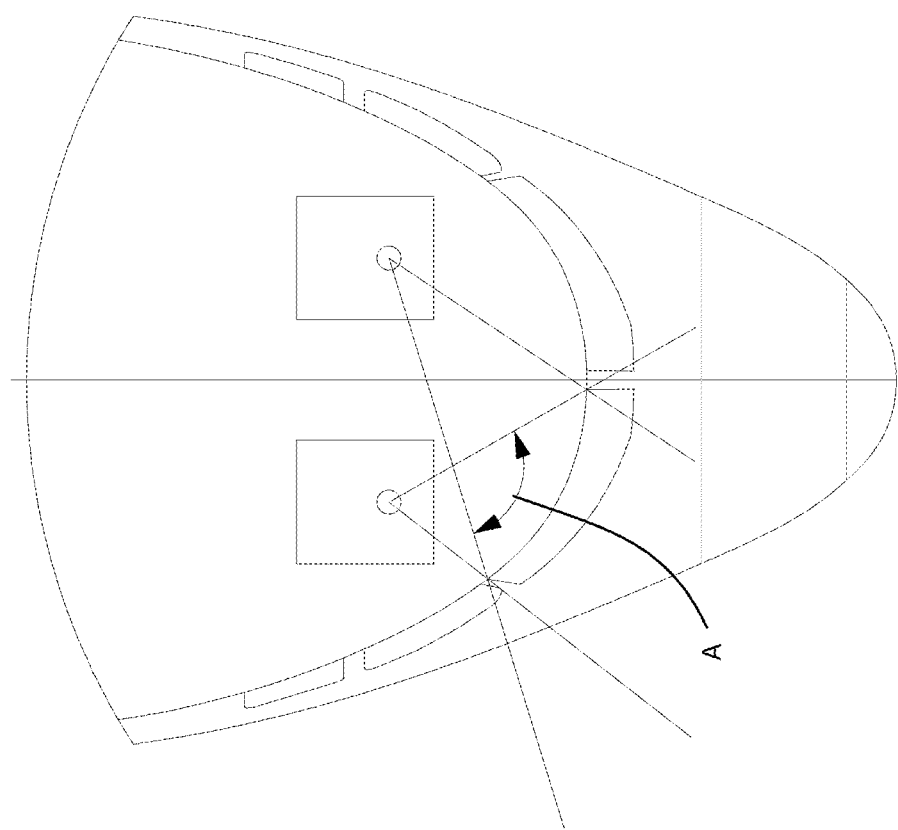
FIG. 5 illustrates horizontal angle coverage for a first aircraft window.
Figure 6:
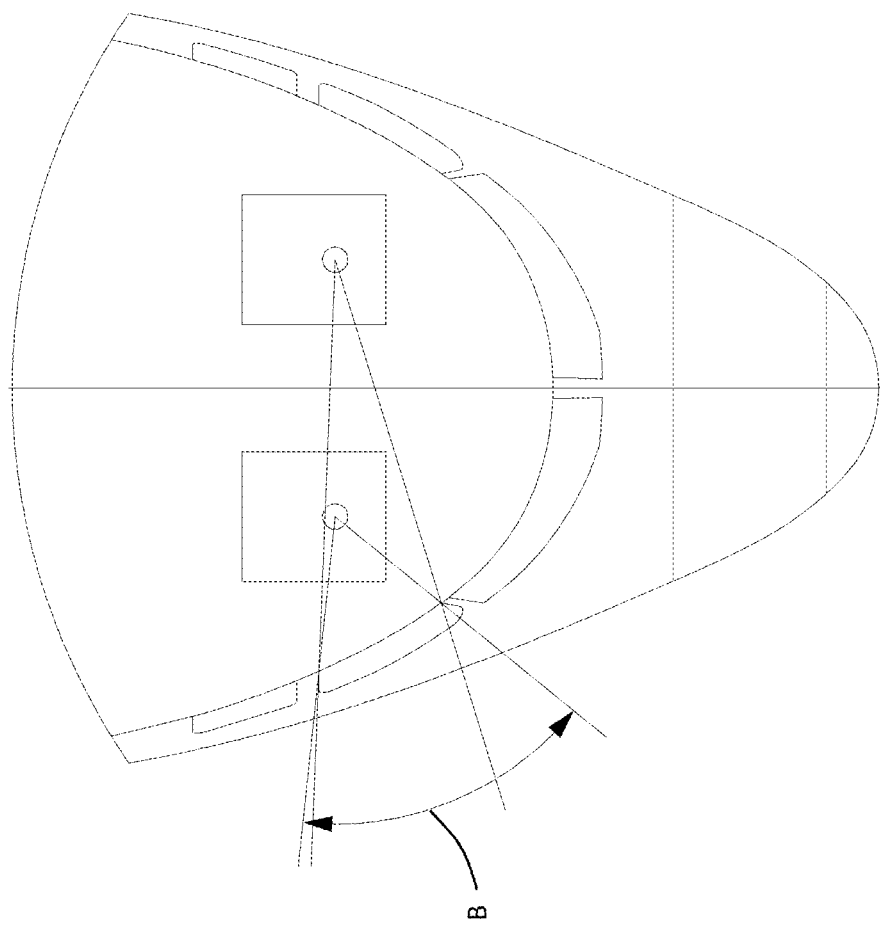
FIG. 6 illustrates horizontal angle coverage for a second aircraft window.
Figure 7:
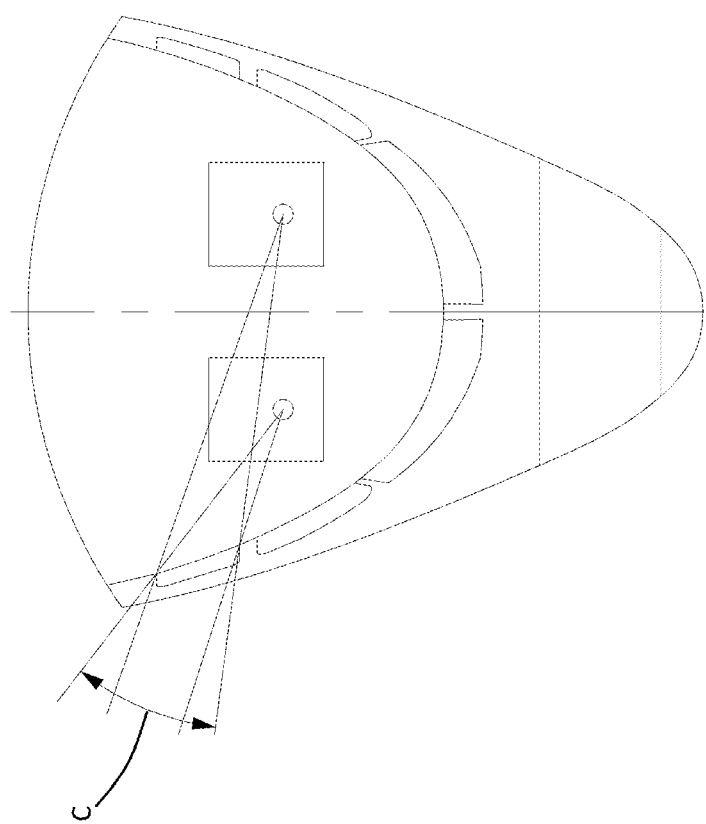
FIG. 7 illustrates horizontal angle coverage for a third aircraft window.
Figure 8:
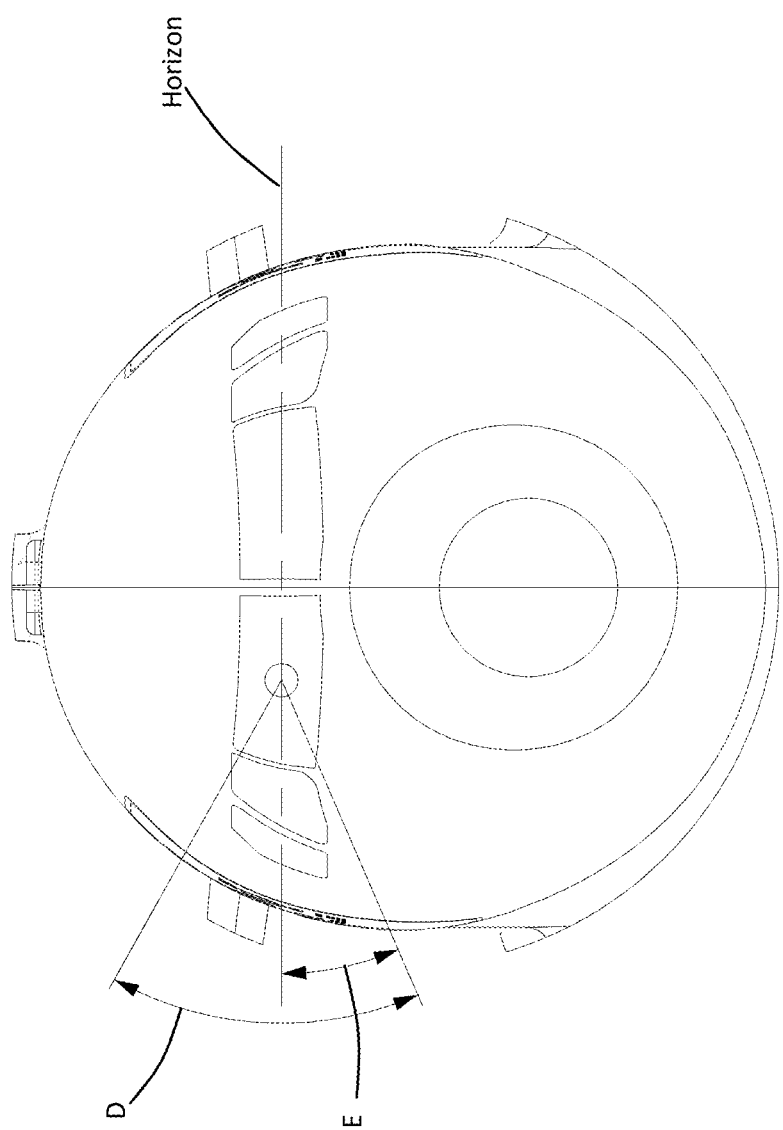
FIG. 8 illustrates vertical angle coverage for a first aircraft window.
Figure 9:
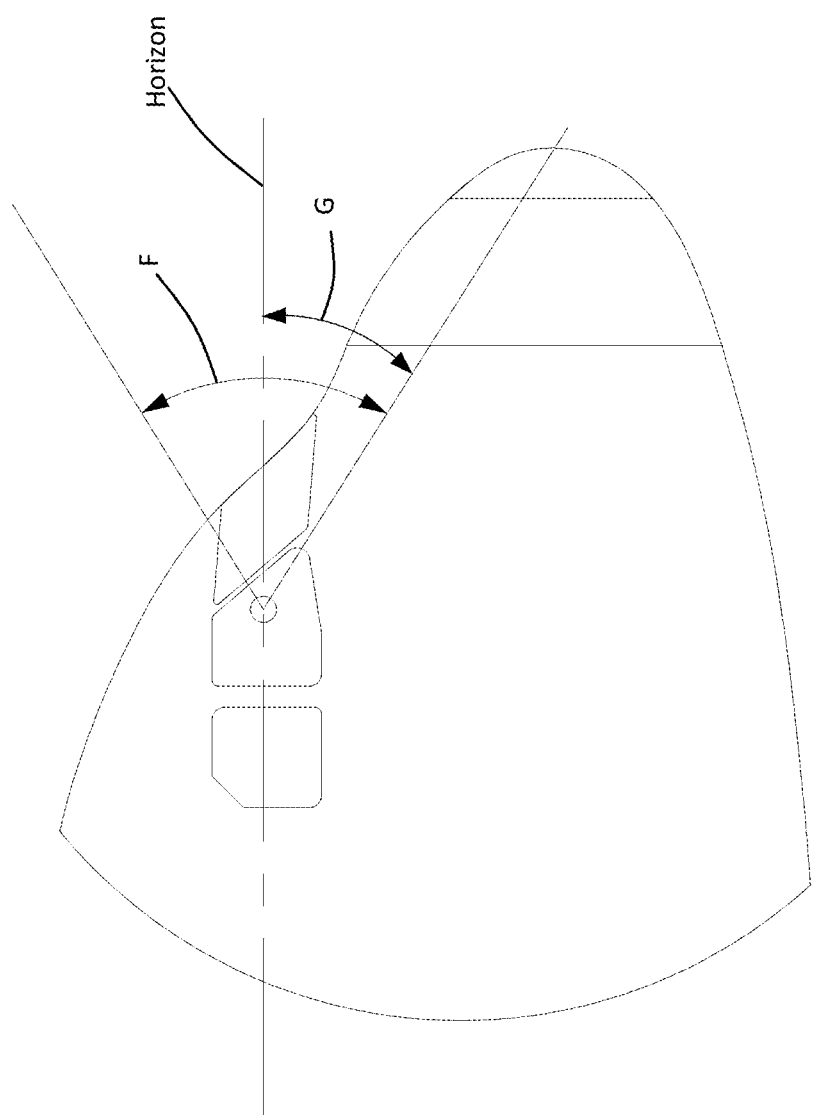
FIG. 9 illustrates vertical angle coverage for a second and third aircraft window.

For the case of a vehicle windscreen such as an aircraft windscreen, the central point between the two eyes can be used to align the radius of curvature of the films. Further, in a vehicle application, the gratings of the metamaterial film can be layered and slanted at various angles, so that they can be optimized to filter laser radiation from a particular direction, typically originating from the ground. FIGS. 5 to 9 illustrate example coverage angles (both horizontal and vertical) for airplane cockpit windows. FIG. 5 shows horizontal angle coverage A for a first window (window 1) of an aircraft. For a particular example of an Airbus™ A330™ aircraft, the angle A may be 85° with the angles relative to an axis X of −15° to +70°. FIG. 6 shows horizontal angle coverage B for a second window (window 2) of an aircraft. For the particular example, the angle B is 90° with the angles relative to the axis X of −50° to +40°. FIG. 7 shows horizontal angle coverage C for a third window (window 3) of an aircraft. For the particular example, the angle C is 28° with the angles relative to the axis X of −72° to −45°. FIG. 8 shows vertical angle coverage D and E for the first window (window 1). In an aircraft situation, the coverage is generally only needed below the horizon, and particularly with angle D between −7° to −63° (D=E in this case) FIG. 9 shows vertical angle coverage F and G for the second and third windows (windows 2 and 3). For the particular example of an aircraft, the required filtering coverage (elevation angle F) in these cases is +12° to −55° for window 2 and +9° to −40° for window 3. The angles mentioned here are intended to take into consideration also the aeronautic behavior of the aircraft during the different phases of flight, as well as the position of potential laser sources originating from the ground.

While metamaterial films can generally be easily laminated to flat and cylindrically curved surfaces, metamaterial films are generally more difficult to laminate to objects having compound (spherical) curvature such as a lens, helmet visor or windscreen. This problem is akin to wrapping a ball with a flat piece of paper. Thermoforming provides a potential solution to the technical challenge.

Figure 10:
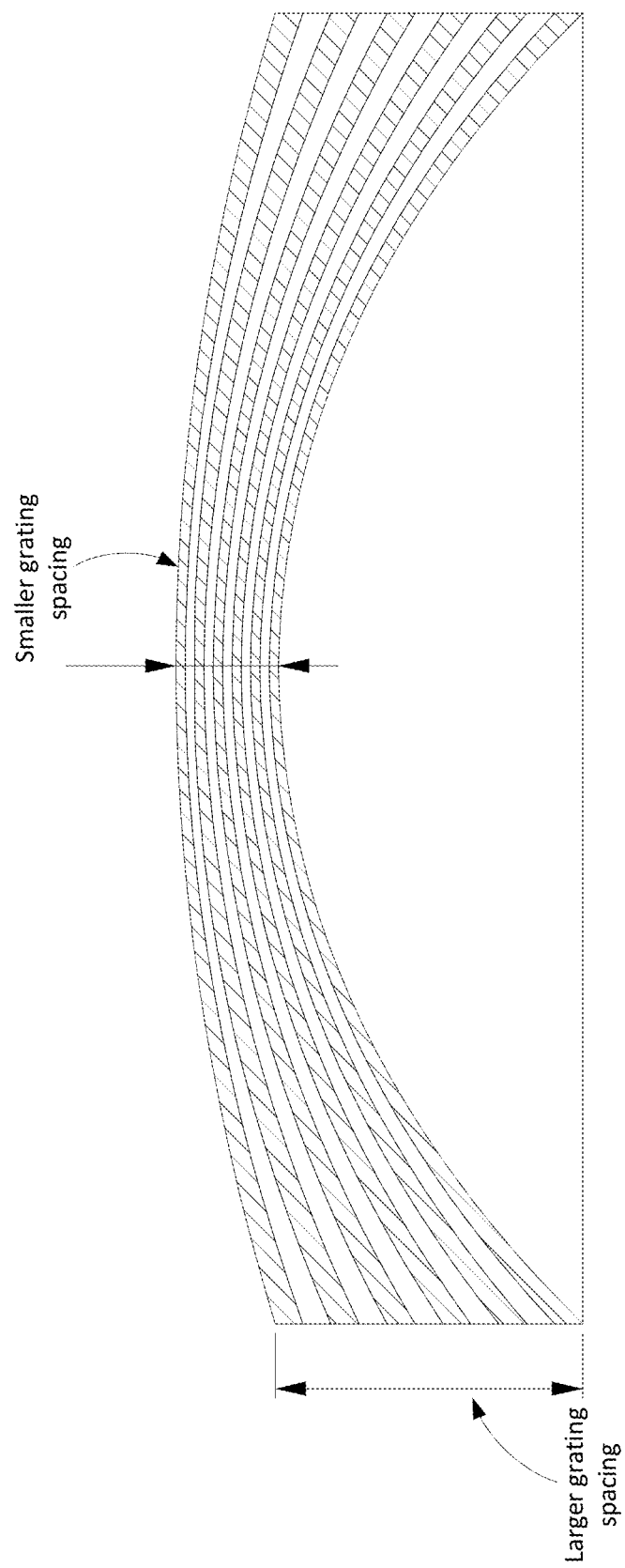
FIG. 10 illustrates a cross-section of a thermoformable metamaterial multilayer optical filter.

A method according to an embodiment herein is to first laminate the one or more metamaterial filters made using holographically patterned subwavelength gratings to a flat substrate e.g. polycarbonate or glass, using an optical adhesive. Both the metamaterial filter and adhesive film can be composed of thermoformable layers e.g. silicone, polymer, etc. This adhesive-metamaterial stack is then cut via a machine to the desired pre-formed shape e.g. a 75 mm diameter circle to form a lens. The stack is then thermoformed via controlled pressure and temperature into the desired geometry e.g. spherical curvature. The adhesive-metamaterial stack and selected substrate are then of spherical curvature and are able to use standard lens finishing processes to integrate into non-flat laser protective eyewear lenses, canopies, windshields or the like. In manufacturing, the metamaterial filter wavelengths can be pre-compensated for the physical stretching during filter formation. FIG. 10 shows a cross-section of a photosensitive polymer layer before thermoforming (with vertical axis enlarged for clarity) that illustrates an example of this type of pre-compensation. In particular, the gratings at the center of the photosensitive polymer layer have a smaller spacing (period) than the gratings at the edge of the photosensitive polymer layer, which have a larger spacing (period). When the metamaterial film is thermoformed, the edges will be stretched and the grating spacing will become uniform on the lens, leading to filtering (laser blocking) of the same wavelength and bandgap across the curved surface. In this way, during the thermoforming process, the film can have a repeatable filter wavelength shift with wavelength pre-compensation of the film such that thermoformed film meets predetermined blocking/filtering requirements. For example, before thermoforming is to be applied, the original metamaterial film's bandgap can be pre-shifted to shorter or longer wavelengths in order to counter-balance the shift caused by the thermoforming process. Further, the bandgap pre-shift of the to-be-thermoformed photosensitive polymer layer does not need to be uniform; but can be radially dependent with gradually smaller shifting away from the center of the film. As such, in the case of a simple lens, a thermoforming process can create a radial metamaterial filter with wavelength dependence to enhance the overall blocking angle. In this case, the shortest wavelengths are in the center of the photosensitive polymer layer and the longer wavelengths are at the periphery.

In a similar way to the pre-compensation for thermoforming, the metamaterial filter may also be pre-compensated based on the intended operating conditions of the environment where the filter will be installed. For example, some aircraft windshields have heating systems and temperature may impact the configuration of the gratings such that the filter can be configured to provide the desired characteristics based on the intended operating environment.

Figure 11:
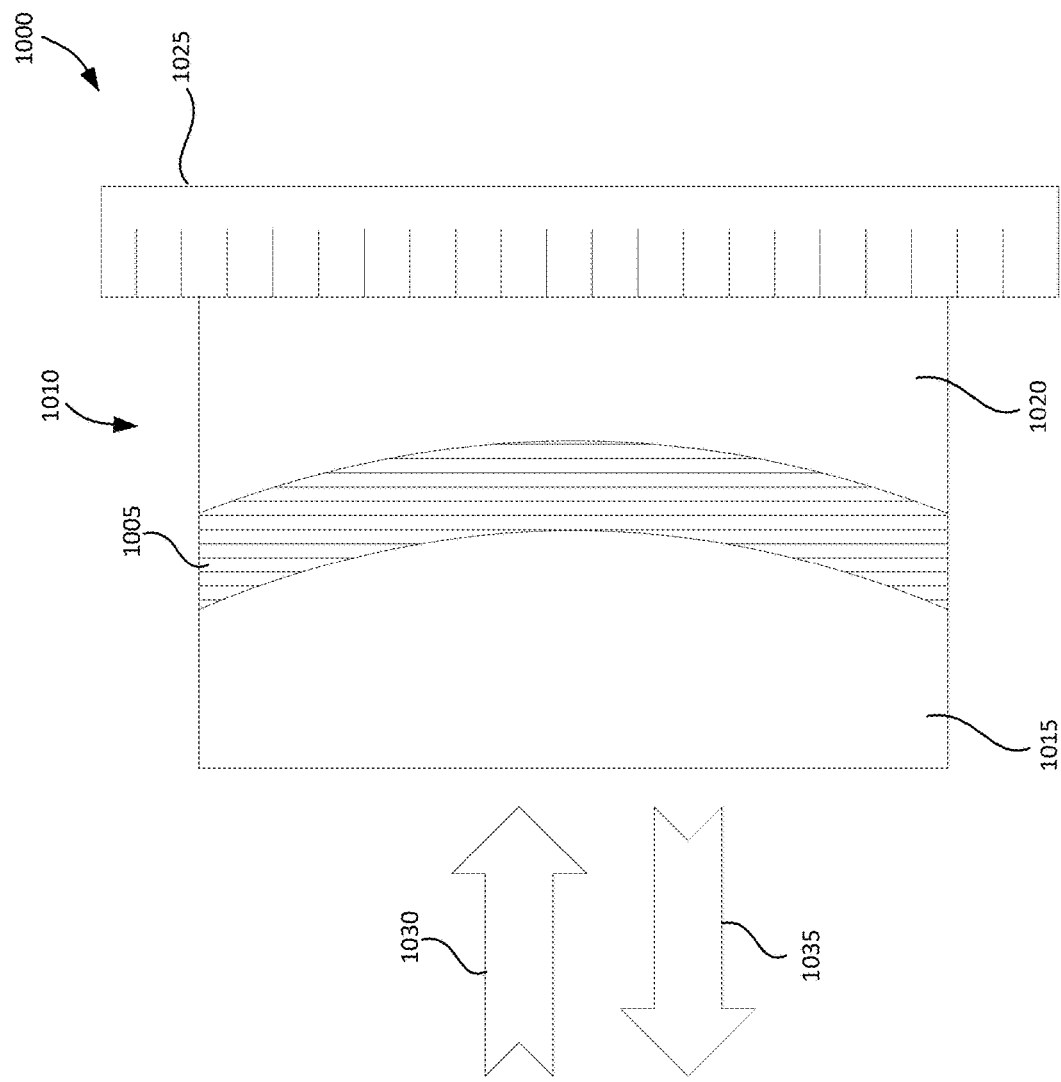
FIG. 11 is a schematic of an embodiment of a system for recording a curved grating.

FIG. 11 illustrates an embodiment of a system 1000 and method for recording a curved grating on a photosensitive polymer layer. In particular, a photosensitive polymer layer 1005 is held in a curved mold 1010 including a first part 1015 and a second mold part 1020. The curved mold could be a cylindrical mold or a spherical mold depending on the type of curvature desired in the grating, i.e. depending on whether the curvature is intended to be two-dimensional or three-dimensional. The curved mold 1010 is placed against a flat mirror 1025. An incident laser beam 1030 is then scanned over the photosensitive polymer layer 1005 and the reflected beam 1035 returns from the mirror to create a reflection grating within the photosensitive polymer layer 1005 from the interference between the incident and reflected beams. In this way, planar interference fringes and a grating are formed within the photosensitive polymer layer region, but since the photosensitive polymer layer is bent, when the photosensitive polymer layer is removed from the mold and flattened these fringes will become curved, as shown in FIG. 3C referred to above.

In order to manufacture the above-described metamaterial filters using holographically patterned subwavelength gratings, different principles can be used. For example, in one embodiment, the exposure to the laser may be made by a moving head carrying the laser or its output through a flexible fiber optic cable, moving over the width or length of the photosensitive polymer layer on a rail, and being scanned by successive offset lines. The exposure may be made directly, in a narrow line across the width or length of the photosensitive polymer layer web, by the passage of the laser head on a carriage powered by, for example, a flexible drive belt on a steel guide rail. The width of the beam, the power of the laser and the distance the photosensitive polymer layer web is advanced between exposures can be determined empirically to achieve a product of high optical density with no visible lines. The laser output head may also be mounted on a motorized rotation stage, so the angle of incidence can be set to compensate the shrinkage of a particular batch of photosensitive polymer layer or expansion created by adhesives/processing to be used in the windshield.

Figure 12:
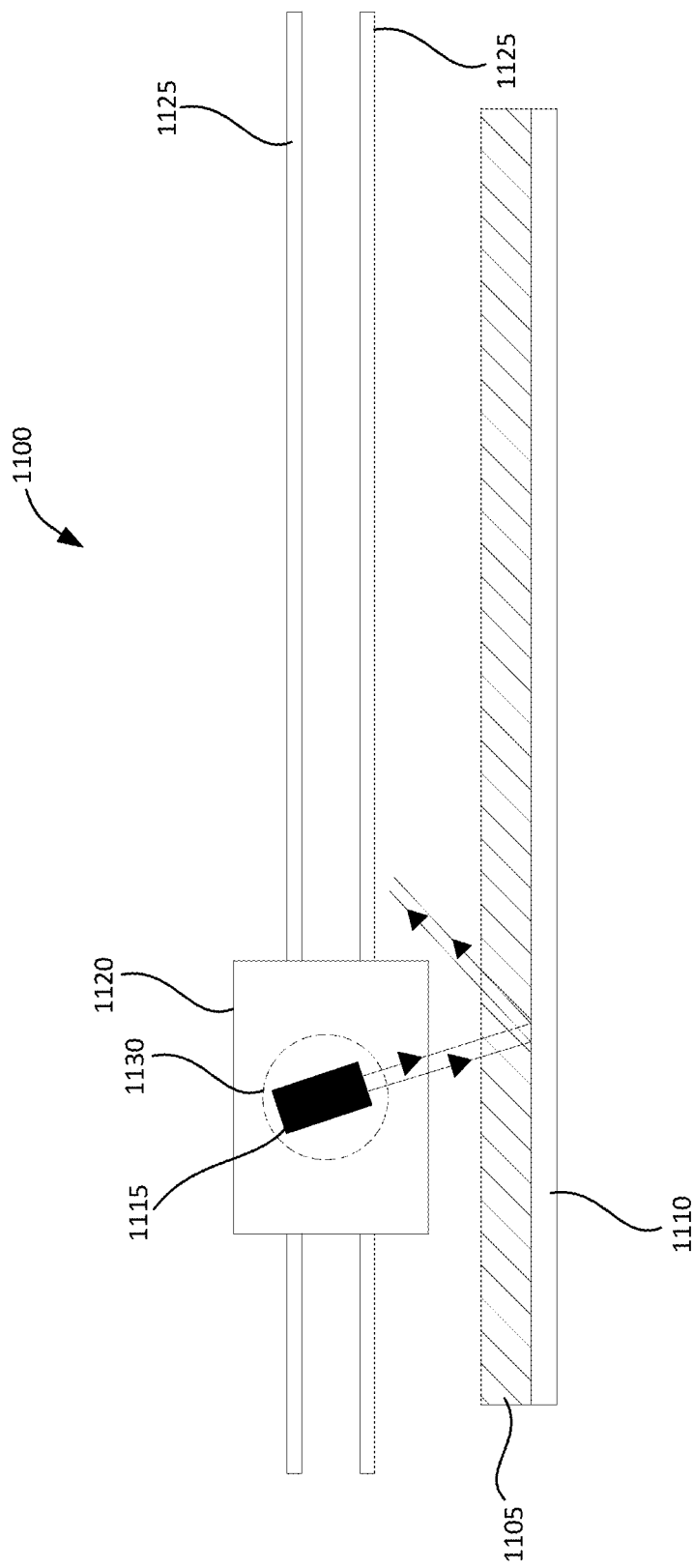
FIG. 12 is a schematic drawing of a system for manufacturing a metamaterial film according to an embodiment herein.

FIG. 12 is a schematic diagram of a system 1100 for manufacturing a metamaterial film filter including one or multiple-layers of complex and conformal gratings. In FIG. 12, a photosensitive polymer layer on a transparent substrate 1105 is adjacent to or applied to a mirror or reflective film 1110. A laser 1115 is attached to a carriage 1120 provided to one or more rails 1125 such that the laser 1115 is configured to move along a longitudinal direction of the photosensitive polymer layer 1105 to process one "line" of the photosensitive polymer layer 1105. In this particular embodiment, a plurality of (three) lasers 1115 and carriages 1120 are provided and in other embodiments a greater or lesser number of lasers and associated equipment may be provided. After completing one pass or "line", the laser 1115 (on carriage 1120) then returns to the beginning of the rails 1125 and the photosensitive polymer layer 1105 is moved perpendicular to the direction of motion of the carriage 1120 so that the laser 1115 can process an additional "line" of the photosensitive polymer layer 1105. In this way, the photosensitive polymer layer 1105 is treated by the laser 1115 at an appropriate level of resolution. In this embodiment, the carriage 1120 also includes a rotation head 1130 configured to allow the laser 1115 to rotate so that the angle of incidence on the photosensitive polymer layer can be adjusted depending on the desired fringe angle. The rotation of the laser may be performed in advance of laser scanning or may be performed during laser scanning in order to adjust the fringe angle for different areas of the photosensitive polymer layer.

Figure 13:
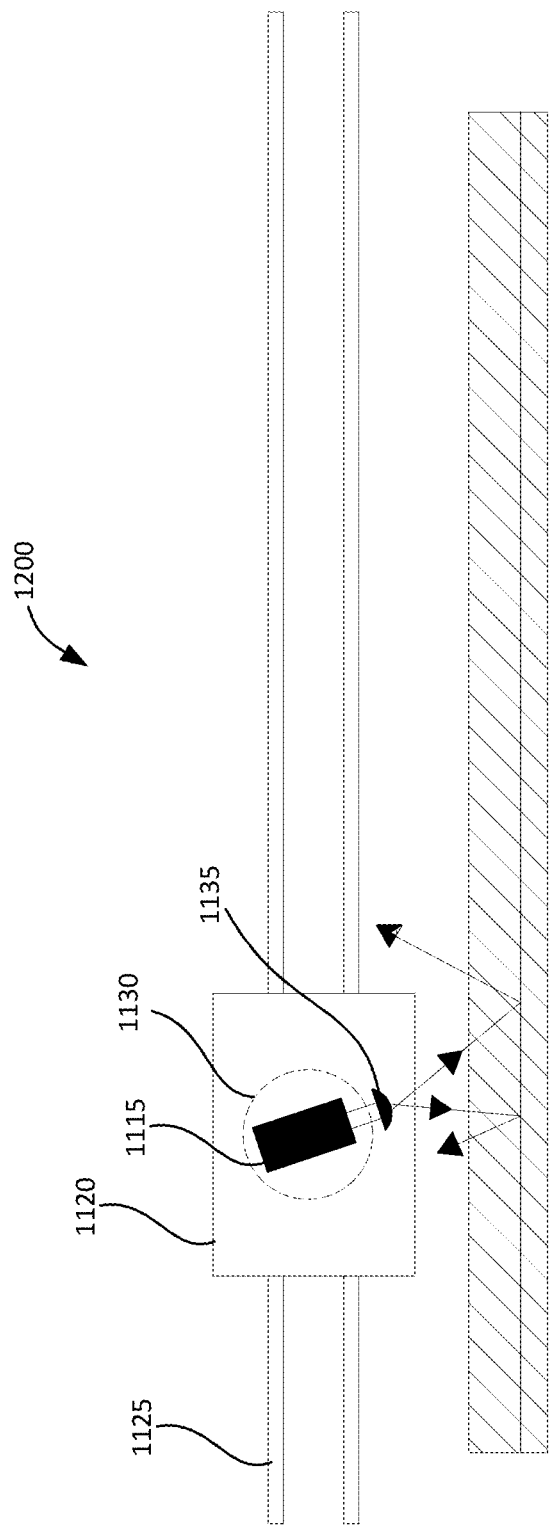
FIG. 13 is a schematic drawing of a system for manufacturing a metamaterial film according to another embodiment herein.

FIG. 13 illustrates another embodiment of the system for manufacturing 1200. In this embodiment, the principle is similar to the embodiment shown in FIG. 12 but with the difference that the laser 1115 includes optional lens 1135 that diverge the laser beam into a 'fan' of light aligned with the direction of travel of the carriage 1120. This "fan" of light creates exposures over a range of angles, inducing a broader angular, and therefore spectral, bandwidth in the resulting filter. The lens 1135 thus provides a control mechanism to vary filter bandwidth.

Figure 14:
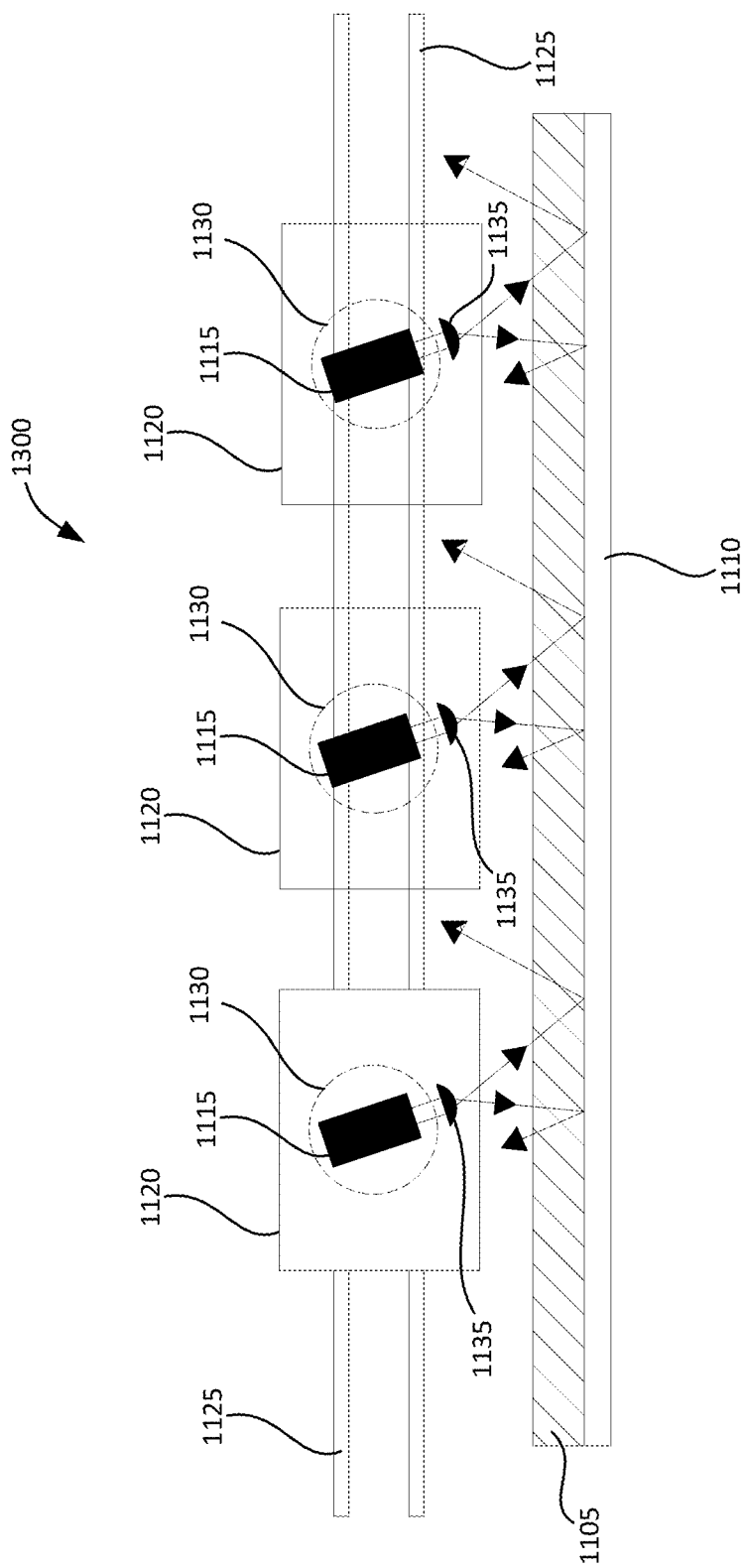
FIG. 14 is a schematic drawing of a system for manufacturing a metamaterial film according to still another embodiment herein.

FIG. 14 is a schematic diagram showing a further embodiment of a system for manufacturing 1300 similar to that in FIG. 13. In this particular embodiment, a plurality of (three) lasers 1115 with lenses 1135 are provided. The use of multiple lasers allows for the recording of multiple gratings on a single photosensitive polymer layer (notch filters) that may, for example, be configured to block different wavelengths. As an example, red, green and blue lasers may be used. It will be understood that, in other embodiments, a greater or lesser number of lasers and associated equipment may be provided.

When using a plurality of lasers, a plurality of notch filters each having different effective wavelengths can be provided to the metamaterial film stack through the process of recording the reflection gratings consecutively or simultaneously using the plurality of laser beams. Although not shown in FIG. 14, the notch filters may be recorded simultaneously by splitting a single recording laser into separate beams and directing said beams onto the photosensitive polymer layer at different angles of incidence. Alternatively, a plurality of lasers of different wavelengths may be combined into a single beam and the combined beam is then directed onto the photosensitive polymer layer at the desired angle of incidence allowing notches of different wavelengths to be recorded simultaneously. Each recorded grating layers with one or multiple notches may be combined by stacking one or more of these grating layers on top of each other to create a complex metamaterial filter stack with multiple notches of different wavelengths, angle, color and optical density control.

In these embodiments, the 'subject beam' for the grating may be supplied by i) internal surface reflection from the final surface of the photosensitive polymer layer or ii) a reflective film or mirror (such as mirror 1110 shown in FIG. 12) temporarily provided to the photosensitive polymer layer, for example by lamination or the like, or iii) a solid mirrored surface such as a metal mirror or coated glass mirror, with the photosensitive polymer layer in optical contact by means of an index matching liquid or the like.

Figure 15:
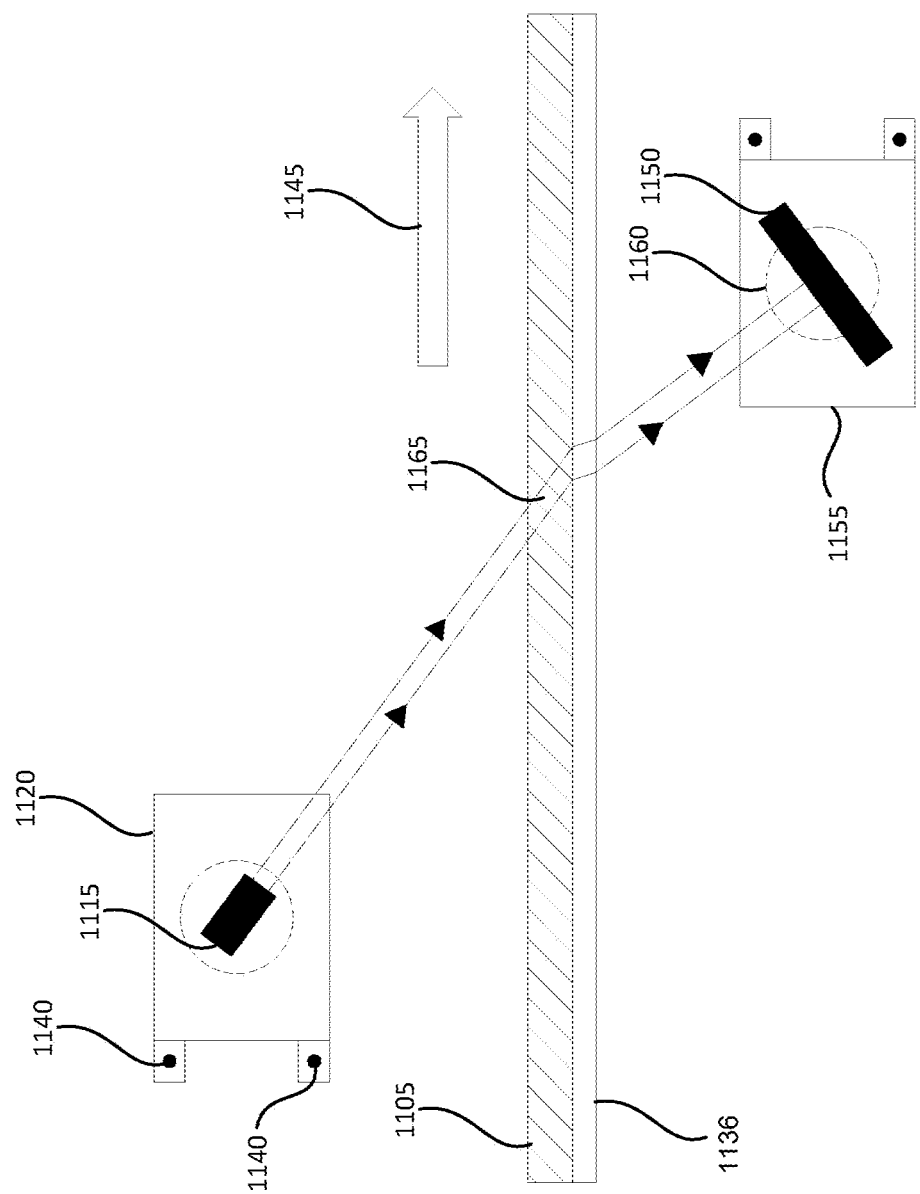
FIG. 15 is a schematic drawing of a system for manufacturing a metamaterial film according to still another embodiment herein.

FIG. 15 illustrates an embodiment of a system for manufacturing 1400 that is configured to provide a slanted-fringe grating. In FIG. 14, the photosensitive polymer layer 1105 is provided on a transparent substrate 1136. The transparent substrate 1136 could be, for example, Polymethyl methacrylate (PMMA), polycarbonate, triacetate (TAC), or the like. Laser 1115 is again attached to carriage 1120 for movement in relation to the photosensitive polymer layer 1105, however, in this embodiment, differing from the embodiments in FIGS. 12 to 14, rails 1140 run in a lateral direction to the photosensitive polymer layer 1105 and the photosensitive polymer layer 1105 is movable in the horizontal direction shown by the arrow 1145. Further, in this embodiment, a mirror 1150 is provided to a second carriage 1155 provided on an opposite side of the photosensitive polymer layer 1105 from the laser 1115. The second carriage 1155 includes a second rotation head 1160 allowing the mirror 1150 to rotate in coordination with the laser 1115 so that the mirror 1150 is angled towards the laser 1115. In this embodiment, live interference fringes are generated by having the mirror 1150 configured to 'retroreflect' the laser beam incident from the laser 1115 onto the top side of the photosensitive polymer layer 1105. Slanted-fringes will be generated where the incident and retroreflection beams cross 1165.

Figure 16:
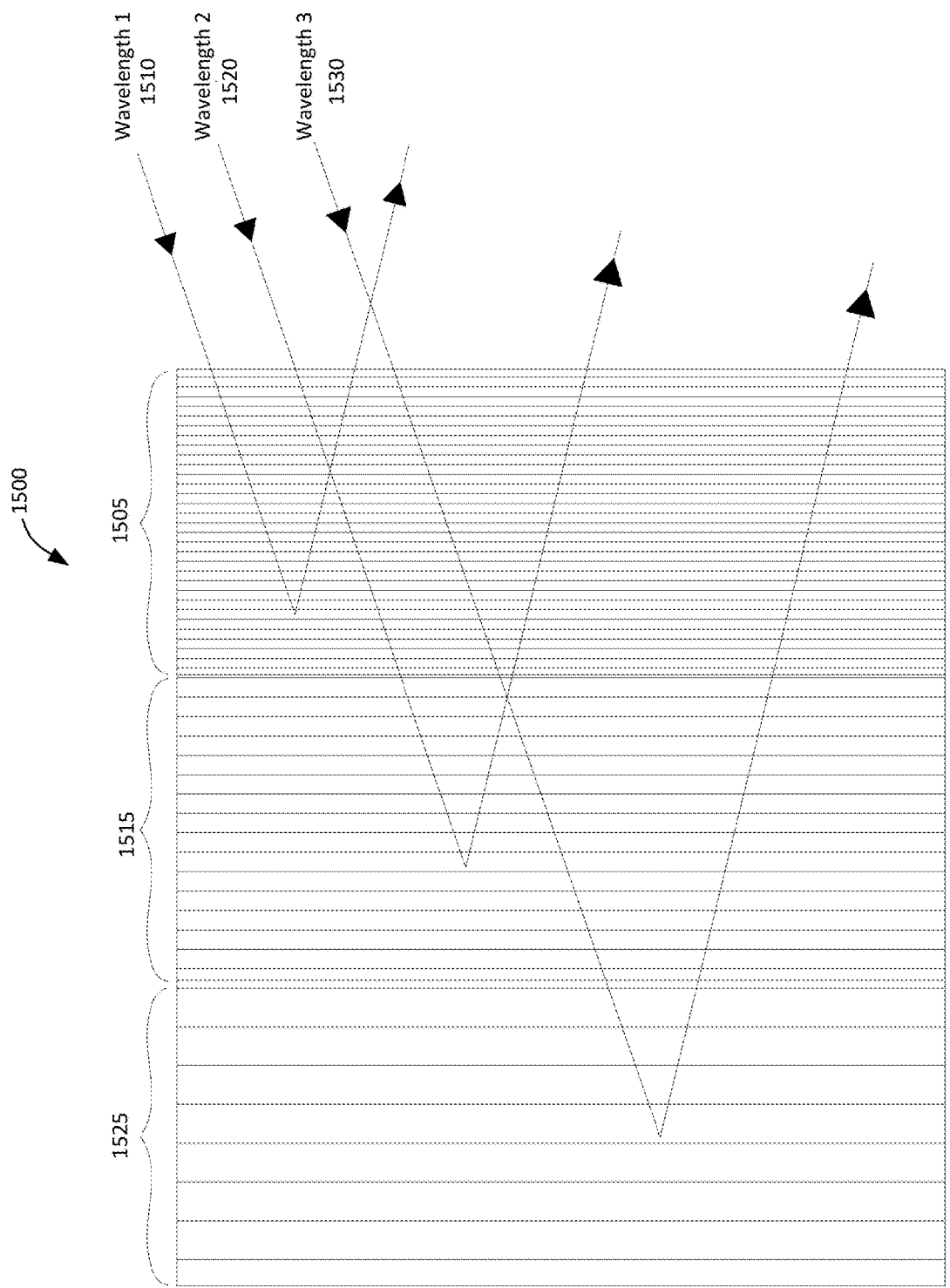
FIG. 16 is an illustration of a multiple stacked photosensitive polymer layers with multiple holographically patterned subwavelength-gratings forming the metamaterial film.

FIG. 16 illustrates the principle of a multi-wavelength metamaterial filter stack 1500. In this stack, there are three recorded gratings of three photosensitive polymer layers, each having a different spacing that is configured to block a different wavelength or wavelength range. In particular, a first layer 1505 is configured to block a first wavelength 1510, a second layer 1515 is configured to block a second wavelength 1520, and a third layer 1525 is configured to block a third wavelength 1530. It will also be understood that the gratings/layers could also overlap in space by using appropriate materials. Thus use of stacked recorded photosensitive polymer layers can increase the effective protection angle and/or negate dispersion effects caused by individual layers and/or improve optical density of the filter. When a pair of slanted grating films are stacked together, these films will generally have the opposite slant.

In addition to the photosensitive polymer grating layers, the metamaterial filter stack may also include other substrate or supporting layers. As noted herein, the substrate or supporting layers may include PMMA, polycarbonate, triacetate (TAC) or the like. Various combinations of photosensitive polymer (PP) grating layers and substrate may be formed, in this case using TAC for example: TAC-PP-PP-TAC; TAC-adhesive-PP-PP-adhesive-TAC; TAC-adhesive-PP-adhesive-PP-adhesive-TAC and the like. The metamaterial filter stack may also include films or coatings for anti-glare, anti-scratch, glazing or the like. The adhesive used in the stack may any appropriate adhesive and may also include graphene.

Figure 17:
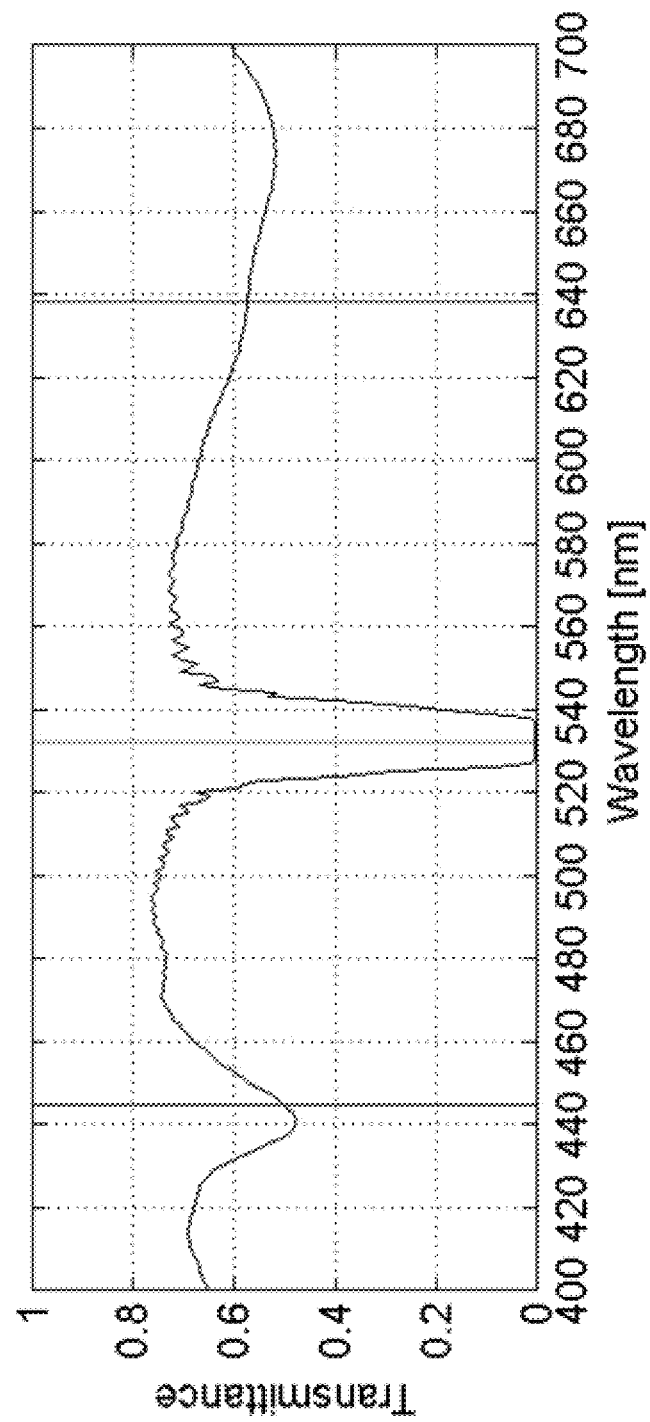
FIG. 17 is a transmittance spectrum for a metamaterial film having one grating.
Figure 18:
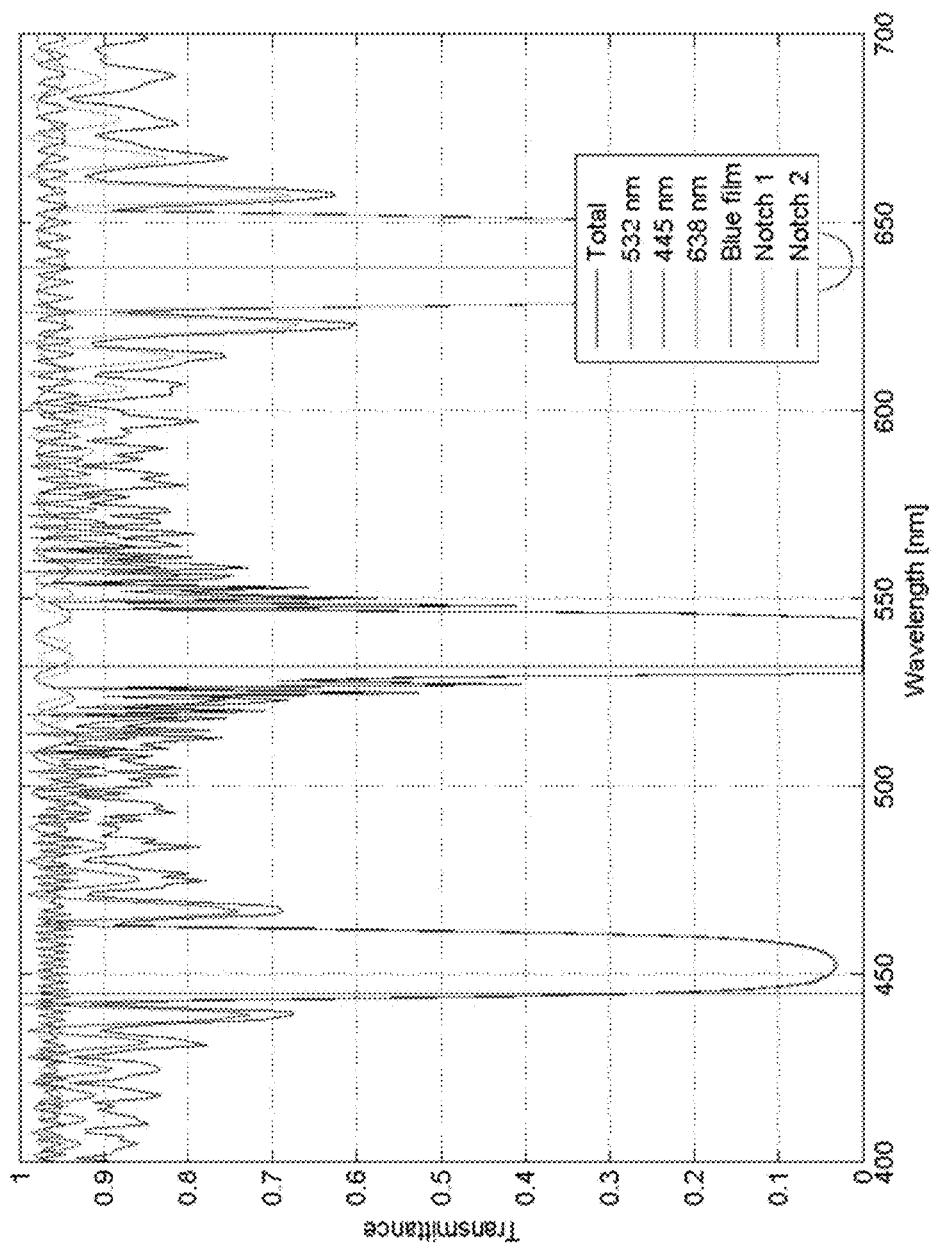
FIG. 18 is a transmittance spectrum for a metamaterial film having multiple gratings.

In some embodiments, a metamaterial filter may be improved by also providing saturation reduction/minimization and/or color balancing for the filter. In particular, a Bragg-type subwavelength holographically patterned grating creates a bandgap and reflects a section of the spectrum in order to block predetermined wavelengths, such as those from a laser. However, this process generally distorts the neutral color of a scene as viewed through such a grating. For example, a grating that blocks 532 nm light will generally appear pink since a green portion of the spectrum is removed. This effect can be counter balanced (color balanced) by also removing some red and blue portion of the spectrum, to produce a color neutral result. This color balancing result can be achieved by adding absorbing dyes, or by adding more holographically patterned gratings that filter out blue and red portions of the spectrum. FIG. 17 shows an example of the transmittance spectrum of a two-layer metamaterial color balanced filter stack, a first layer being a holographically patterned grating at 532 nm and the second layer being a polycarbonate sheet doped with blue and red absorbing dyes with predetermined concentrations to balance the color of the overall metamaterial filter stack. FIG. 18 shows an example of the predicted transmittance spectrum when a metamaterial color balanced filter stack using three holographically patterned gratings (blue, green and red) are used (as illustrated in FIG. 16). The resulting metamaterial filter stack exhibits excellent color balancing properties and, in addition to the green laser (similar to the filter of FIG. 17), this type of filter can also can block red and blue lasers (these wavelengths are shown with vertical lines).

Figure 19:
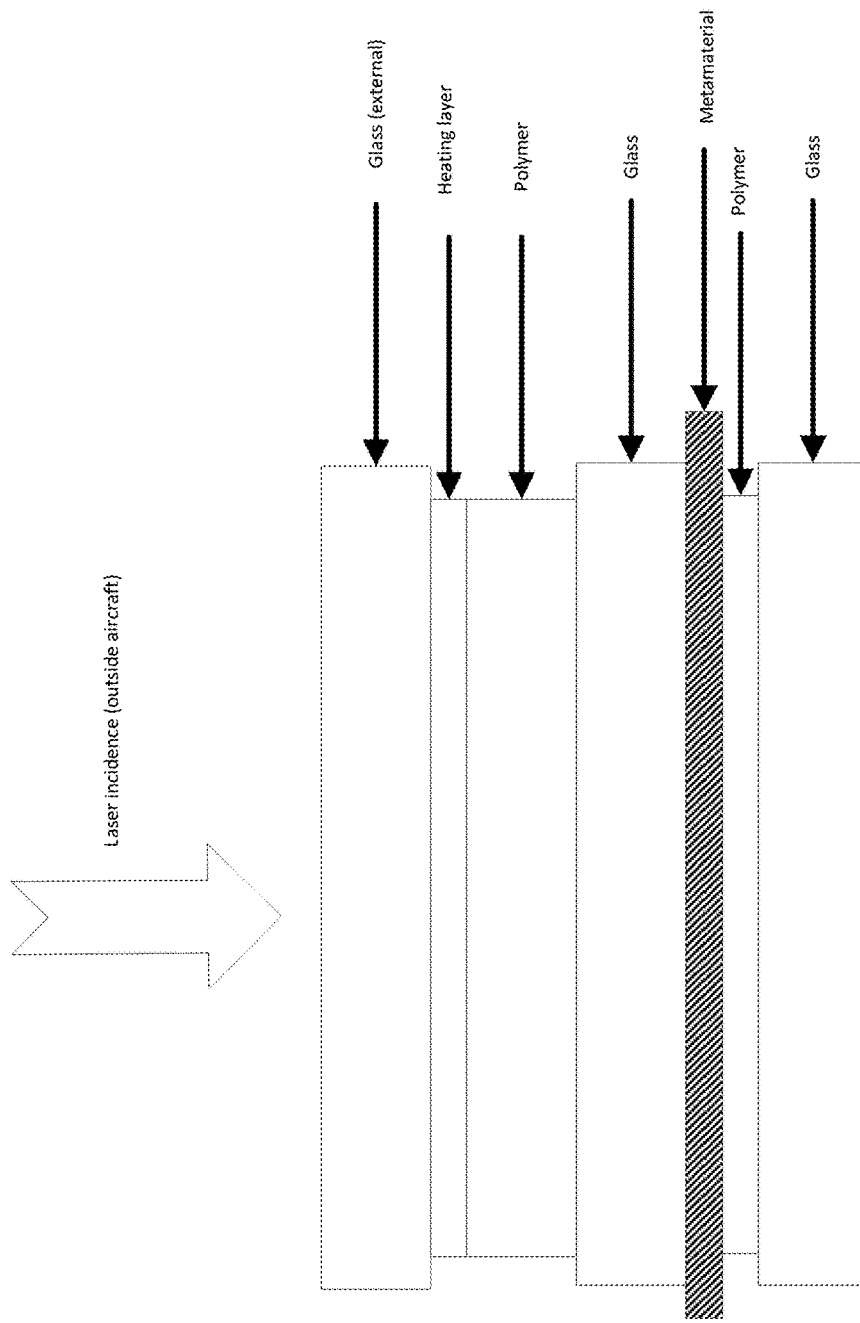
FIG. 19 illustrates various components of an aircraft windshield according to an embodiment herein.
Figure 20:
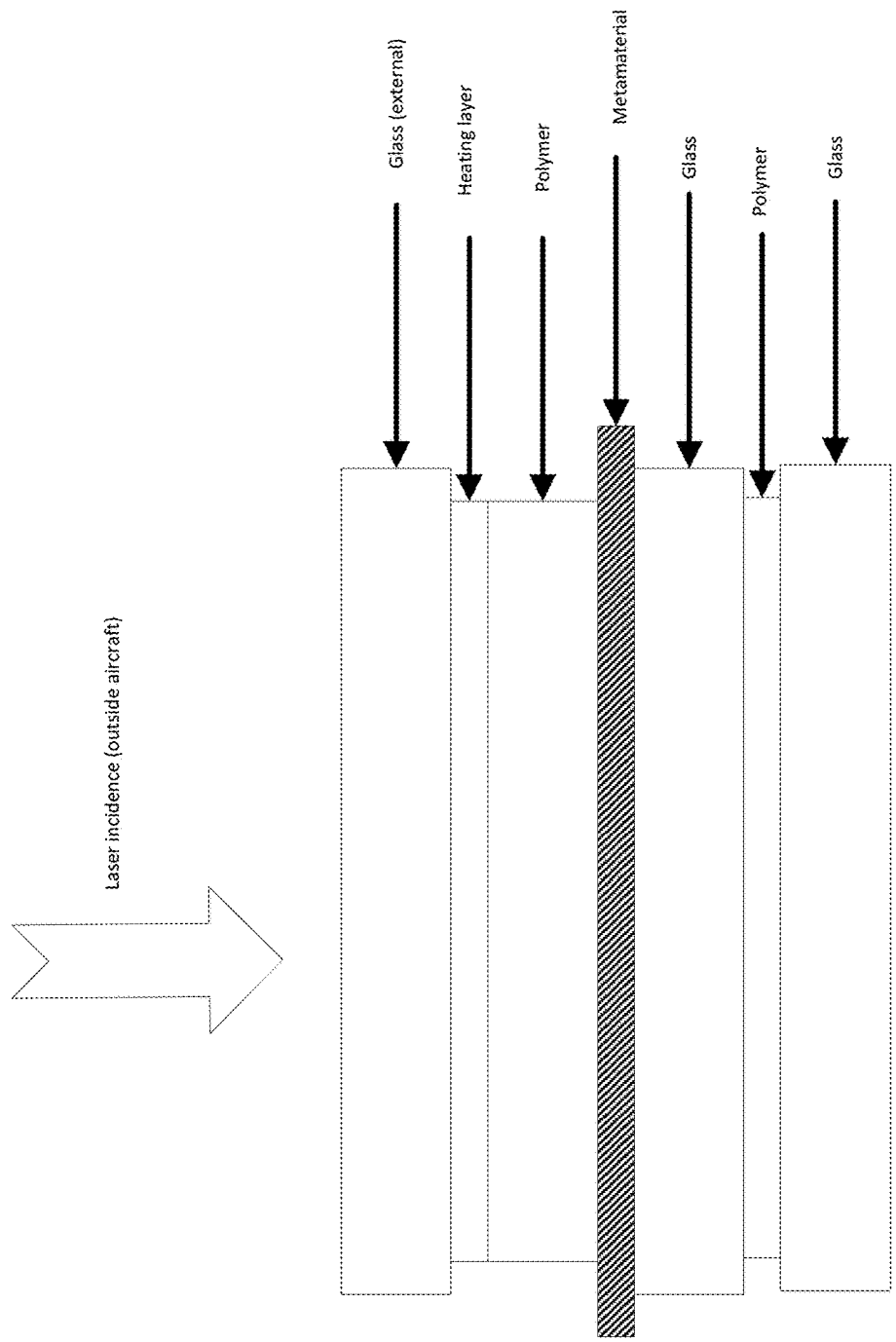
FIG. 20 illustrates various components of an aircraft windshield according to another embodiment herein.

As noted herein, the metamaterial film may be used/applied in various locations in relation to other components of an aircraft windshield. In some cases, the metamaterial may be used/applied on the interior of the windshield while in others, the metamaterial may be used/applied within a windshield structure. FIG. 19 and FIG. 20 show two alternate configurations of windshields.

In the preceding description, for purposes of explanation, numerous details are set forth in order to provide a thorough understanding of the embodiments. However, it will be apparent to one skilled in the art that these specific details may not be required. In other instances, well-known structures may be shown in block diagram form in order not to obscure the understanding. For example, specific details are not provided as to whether elements of the embodiments described herein are implemented as a software routine, hardware circuit, firmware, or a combination thereof.

Embodiments of the disclosure or components thereof can be provided as or represented as a computer program product stored in a machine-readable medium (also referred to as a computer-readable medium, a processor-readable medium, or a computer usable medium having a computer-readable program code embodied therein). The machine-readable medium can be any suitable tangible, non-transitory medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration information, or other data, which, when executed, cause a processor or controller to perform steps in a method according to an embodiment of the disclosure. Those of ordinary skill in the art will appreciate that other instructions and operations necessary to implement the described implementations can also be stored on the machine-readable medium. The instructions stored on the machine-readable medium can be executed by a processor, controller or other suitable processing device, and can interface with circuitry to perform the described tasks.

The above-described embodiments are intended to be examples only. Alterations, modifications and variations can be effected to the particular embodiments by those of skill in the art without departing from the scope, which is defined solely by the claims appended hereto.

What is claimed is:

1. A method of manufacturing an optical filter configured to block a predetermined bandwidth of electromagnetic radiation at a predetermined angle, the method comprising:
   providing a photosensitive polymer layer disposed between a laser and a mirror; and
   scanning the laser over the photosensitive polymer layer and moving the mirror in coordination with the laser so that the mirror is angled towards the laser to retroreflect the laser light to the photosensitive polymer layer such that a holographically patterned subwavelength grating is created within the photosensitive polymer layer by interaction between the laser light and light retroreflected from the mirror, the holographically patterned subwavelength grating having a spacing dependent on the predetermined bandwidth of electromagnetic radiation.

2. A method for manufacturing according to claim 1, wherein the scanning comprises moving one or more of the laser, the photosensitive polymer layer and the mirror.

3. A method for manufacturing according to claim 1, wherein the photosensitive polymer layer has a filter wavelength pre-compensation including gratings having a smaller spacing at a center of the photosensitive polymer layer than gratings at an edge of the photosensitive polymer layer, the method further comprising thermoforming the photosensitive polymer layer to have a repeatable filter wavelength shift.

4. A method for manufacturing according to claim 3, wherein the original photosensitive polymer layer's bandgap is pre-shifted to longer wavelengths in order to counterbalance the shift caused by the thermoforming process.

5. A method for manufacturing according to claim 4, wherein the bandgap pre-shift is radially dependent with gradually smaller shifting away from the center of the photosensitive polymer layer.

6. A method for manufacturing an optical filter, comprising:
   manufacturing two or more holographically patterned subwavelength gratings, each formed on a single photosensitive polymer layer, and each according to the method of claim 1; and
   combining the two or more holographically patterned subwavelength gratings into a multi-layered optical filter stack, to allow control of angle, bandgap, optical density and color balance of the multi-layered optical filter stack.

7. A method for manufacturing according to claim 6, further comprising using an adhesive to bond the two or more holographically patterned subwavelength gratings in the multi-layered optical filter stack, wherein the adhesive comprises graphene.

8. A method for manufacturing according to claim 1, wherein the photosensitive polymer layer is applied to a substrate and the photosensitive polymer layer applied to the substrate is placed between the laser and the mirror.

9. A method for manufacturing according to claim 1, wherein the optical filter comprises a holographically patterned subwavelength grating, the grating comprising non-conformal fringes configured to block the predetermined bandwidth of electromagnetic radiation at the predetermined angle.

10. A method for manufacturing according to claim 9, wherein the holographically patterned subwavelength grating of the optical filter is curved in order to maximize an effective angle of protection.

11. A method for manufacturing according to claim 9, wherein the holographically patterned subwavelength grating of the optical filter comprises a plurality of gratings, wherein each of the gratings is configured to block a different predetermined bandwidth of electromagnetic radiation.

12. A method of manufacturing according to claim 11, wherein at least one of the plurality of holographically patterned subwavelength gratings of the optical filter is provided to color balance the filter.

13. A method of manufacturing according to claim 11, wherein the plurality of holographically patterned subwavelength gratings of the optical filter are configured to selectively block at least one of approximately 405 nm, 445 nm, 520 nm, 532 nm, 635 nm, 650 nm wavelengths.

14. A method of manufacturing according to claim 9, wherein the photosensitive polymer layer of the optical filter is shaped for a transparent substrate using thermoforming and the photosensitive polymer layer is pre-configured to allow for changes to the photosensitive polymer layer during thermoforming.

15. A method of manufacturing according to claim 9, wherein the photosensitive polymer layer is infused with a dye selected to color balance the filter.

16. A method of manufacturing according to claim 9, wherein the optical filter includes a substrate that contains a dye selected to color balance the filter.

17. A method of manufacturing according to claim 9, wherein the optical filter comprises two or more transparent substrates and the photosensitive polymer film is positioned between at least two of the two or more transparent substrates.

18. A method of manufacturing according to claim 9, wherein the predetermined angle of the non-conformal fringes is up to 75 degrees below a normal axis of the filter.

19. A method of manufacturing according to claim 9, wherein the optical filter further comprises a transparent substrate and an adhesive bonding the transparent substrate and photosensitive polymer layer wherein the adhesive comprises graphene.

20. A method of manufacturing according to claim 9, wherein the optical filter includes a transparent substrate on which the photosensitive layer is disposed.

21. A method of manufacturing according to claim 20, wherein the transparent substrate is selected from one of the following:
   a window;
   eyewear; and
   a visor.

* * * * *